United States Patent [19]

Maurer

[11] Patent Number: 5,615,674
[45] Date of Patent: Apr. 1, 1997

[54] CLAMPING CONTACT CONNECTION

[75] Inventor: Andreas Maurer, Stuttgart, Germany

[73] Assignee: Hewlett-Packard Company, Palo Alto, Calif.

[21] Appl. No.: 408,201

[22] Filed: Mar. 22, 1995

[30] Foreign Application Priority Data

May 17, 1994 [DE] Germany .................... 44 17 200.1

[51] Int. Cl.⁶ ................................. A61B 5/0408
[52] U.S. Cl. ................ 128/642; 439/269.2; 439/660; 439/909
[58] Field of Search .................. 128/639, 642; 439/269.2, 592, 593, 660, 909

[56] References Cited

U.S. PATENT DOCUMENTS

| Re. 28,990 | 5/1976 | Hon et al. .................. | 128/2.06 E |
|---|---|---|---|
| 4,301,806 | 11/1981 | Helfer ........................ | 128/642 |
| 5,046,965 | 9/1991 | Neese et al. ................ | 128/642 |
| 5,168,876 | 12/1992 | Quedens et al. ............ | 128/642 |
| 5,199,432 | 4/1993 | Quedens et al. ............ | 128/642 |
| 5,388,579 | 2/1995 | Dowd et al. ................ | 439/909 |

FOREIGN PATENT DOCUMENTS

| 0484107 | 5/1992 | European Pat. Off. . |
|---|---|---|
| 4228351 | 8/1992 | Germany . |

*Primary Examiner*—Lee S. Cohen

[57] ABSTRACT

A clamping contact connection is provided for contacting a fetal scalp electrode, which is fixable to the head of the fetus by means of a tubular insertion, aid with a leg plate fittable to the expectant mother. The clamping contact connection comprises a first contact element, which is at least partly wedge-shaped or tapers and has at least two outer contact faces, and a second contact element openable on its front end and which has at least two openable jaws with inner contact faces. During contacting, the jaws of the second contact element engage round at least the wedge-shaped or tapering area of the first contact element. Additional holding elements prevent the unintentional separation of the clamping contact connection. The connection permits an easy manufacture of the individual elements, good cleaning, safe and rapid connection and also separation of the contact elements, as well as adequate protection against accidental, incorrect mains connection.

8 Claims, 3 Drawing Sheets

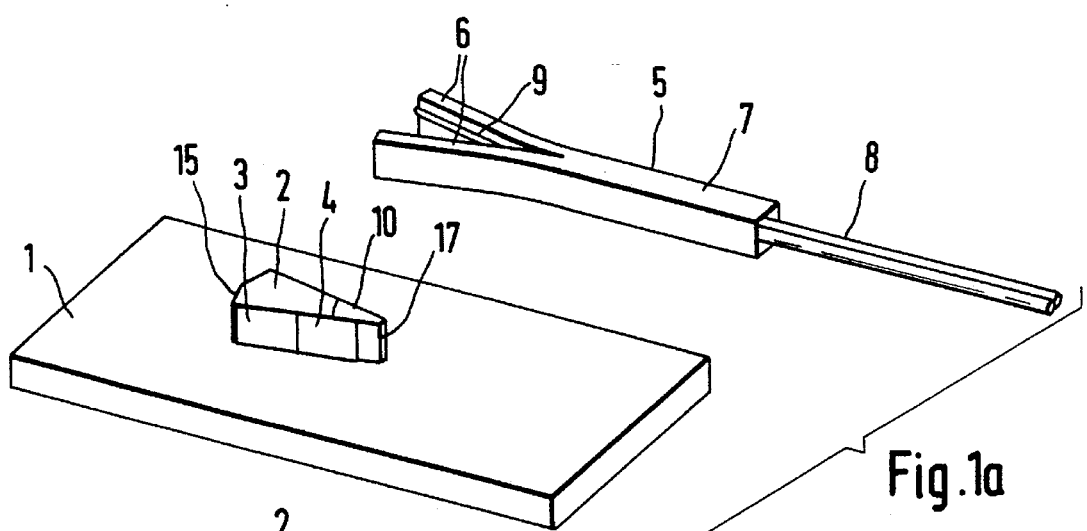
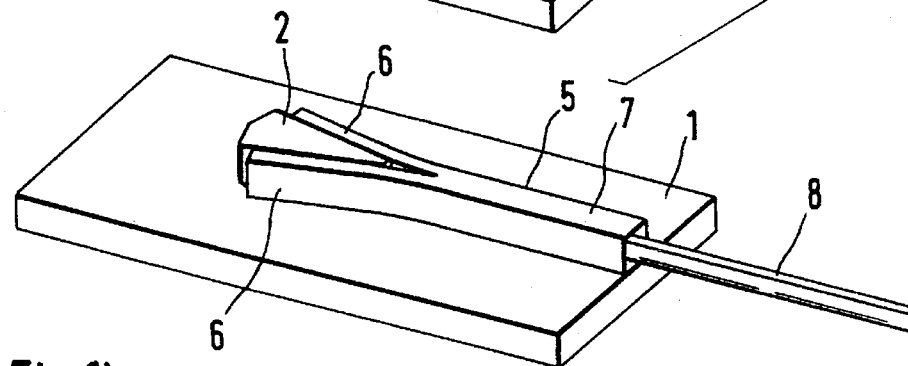
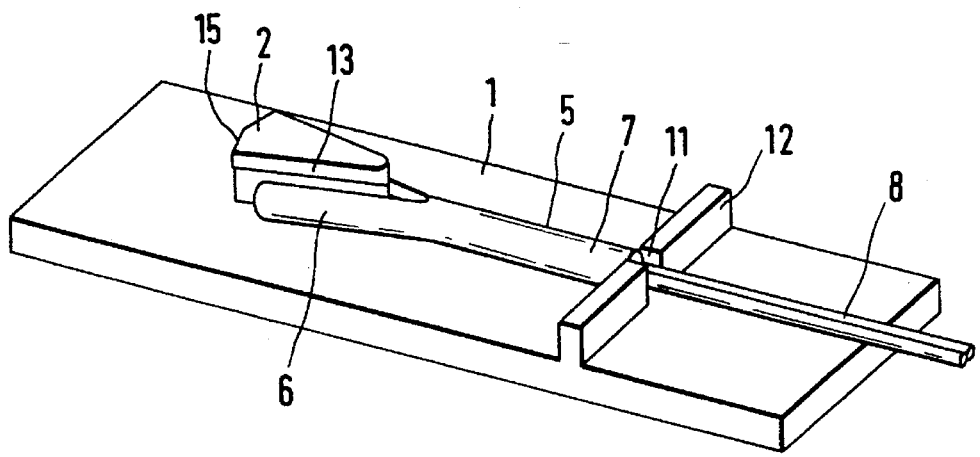

CLAMPING CONTACT CONNECTION

BACKGROUND OF THE INVENTION

The present invention relates to a clamping contact connection for the electrical connection of a fetal scalp electrode to a leg plate fixable to the expectant mother.

In order to record the heart rate of the unborn fetus before and during birth, use is made of scalp electrodes, which are provided on the side thereof facing the fetus head with one or two spiral wires, which are turned into the fetal scalp. For this purpose use is normally made of a vaginal introduction aid with an inner and an outer tube, which facilitates the application of the scalp electrode. The electrode head with the spiral wire or some other fastening means is located in the outer tube at its end facing the fetus. The electrode head and the inner tube have a nonrotary, but detachable connection.

For applying the electrode the doctor firstly guides the outer tube into the birth canal until it contacts the scalp of the fetus. Whilst holding the outer tube the other hand is used for sliding forwards the inner tube until the spiral wire fitted to the electrode head comes into contact with the head of the fetus. Subsequently the inner tube is turned, so that the spiral electrode perforates the fetal scalp and penetrates the same. The inner tube can now be retracted, because the electrode head and the inner tube are not fixed to one another in the axial direction. Subsequently the outer tube is also retracted. Scalp electrodes and introduction mechanisms are known per se and are frequently mentioned in patent literature, e.g. in U.S. Pat. Re. No. 28 990, U.S. Pat. No. 4,301,806 or DE 4,228,351 C1.

The connecting wire of the electrode head is guided through the inner tube and following the drawing out of the two tubes remains in the birth canal and is then connected to a corresponding monitoring instrument, e.g. a cardiotocograph. For this purpose the connecting wires are connected to a so-called maternal leg plate, which is fixed to the leg of the expectant mother. The maternal leg plate is essentially a small box with a conductive base, which produces a galvanic contact with the body of the mother and is intended to prevent extreme potential fluctuations. In turn the leg plate is connected by a cable to the cardiotocograph.

The connection of the wires to the leg plate must be such that an the one hand a reliable electrical contact is provided, but on the other so that the connection can be rapidly detached, so that during birth the relatively heavy leg plate does not tear the spiral electrode out of the scalp of the baby and consequently cause serious injury. In addition, it must be easy to clean the leg plate, because it is fixed to the thigh of the mother and consequently during birth comes into contact with blood or other body liquids. The electrical connection of the leg plate and wire ends must be such that it can be brought about with a minimum of manipulations. In addition, the risk of an erroneous connection to sockets carrying mains voltage must be prevented. The contacting device on the wires of the scalp electrode must pass through the introduction tube, because the latter is, as stated, retracted after fitting.

Hitherto clamping devices have been fitted to the leg plate and in these are clamped already insulated ends of the wires. In this case one hand must be used for operating the clamping device and the other for introducing the wire into the clamping device. For the clamping device the leg plate must be movable and/or have parts sliding on one another. These transitions or junctions are generally difficult to clean, because liquid can be deposited by capillary action and is very difficult to remove. If they come into contact with the mains voltage, the free wire ends can endanger the baby and/or mother. Another connection of the scalp electrode to the leg plate is known from EP 484,107 A1, in which a plug or a socket is connected to the wire ends of the scalp electrode and is then connected to a corresponding counterpart in the leg plate. Although with this plug connection a very simple connection of electrode and leg plate can be obtained by plugging action, the contacts are free and can dome into contact with parts carrying the mains voltage. There is a dirtying risk as a result of the openings in the leg plate for receiving the plug or the socket and said openings are not easy to clean.

The problem of the present invention is therefore to propose a detachable electrical connection of the scalp electrode to the leg plate, which is improved compared with the prior art with respect to fitting, detachability, cleaning and safety.

SUMMARY OF THE INVENTION

According to the invention this problem is solved by a clamping contact connection having the features of the main claim. The clamping contact connection comprises a first contact element, which is constructed in an at least wedge-shaped or tapering manner and in this area has at least two outer contact faces, as well as a second contact element openable at its front end, which has at least two openable jaws with inner contact faces. One contact element is connected to the scalp electrode, whereas the other element is fixed to the leg plate. It is fundamentally possible to connect both the first wedge-shaped or tapering contact element and the second openable contact element to the scalp electrode, so that the in each case other element is fitted to the leg plate. The contact element fitted to the scalp electrode must have an external diameter such that it can be passed through the inner tube. It is therefore designed as an elongated, substantially cylindrical part with a gripping area for handling the contact element and a contact area, in which either the openable jaws are located or which has a wedge-shaped or tapering construction.

During contacting the jaws of the second contact element engage round at least the wedge-shaped or tapering area of the first contact element, so that the inner contact faces of the second contact element contact the outer contact faces of the first contact element and the electrical connection is formed. Additional holding elements prevent an unintentional separation of the connection. The second openable contact element can be constructed in clamp-like manner with at least two jaws and have on its end holding hooks, which engage in corresponding indentations on the first contact element. A further possibility consists of the holding hooks engaging round the first contact element, so that an axial detachment of the clamping contact connection is not possible. Spring elements located within the second contact element can ensure a corresponding contact pressure or the closing of the jaws after drawing off. As a function of the design the drawing off of the second contact element can be take place by opening the jaws or by a movement perpendicular to the longitudinal axis of the clamping contact connection However, the first contact element can also be fixed in spaced manner with respect to the leg plate, so that a second openable contact element completely engaging round the front area of the first contact element can be fitted on. With this design it is possible to have a plurality of contact faces, particularly when using a conically constructed first contact element.

The advantage of the clamping contact connection constructed according to the invention is that it has a simple construction and is therefore also easy to clean, ensures easy operation and offers the necessary patient safety.

Further advantageous developments can be gathered from the subclaims. To prevent unitentional detachment of the clamping contact connection, according to a preferred embodiment hooks are provided as holding elements on the jaws of the second contact element and either engage in corresponding indentations on the first contact element or engage round said first contact element. In order to facilitate manufacture of the connection, advantageously the hooks are shaped in such a way that on the front end of the second contact element is formed a central depression with respect to the jaws, in which during assembly of the connection passes the tip of the first contact element, so as to then open the second contact element due to the wedge-shaped design.

According to a preferred embodiment the first contact element is constructed as a wedge, which is fixed to the leg plate and has a plan view, which essentially corresponds to an acute-angled triangle, the corresponding acute-angled lateral faces being constructed as contact faces and on contacting the holding elements of the second contact element are supported on the back of the wedge. This construction is particularly easy to manufacture and particularly easy to clean. The second contact element can be engaged on the wedge and securely fixed thereto by means of hooks. In order to prevent an accidental upward sliding away from the base surface, preferably the wedge surface remote from the leg plate projects at least in this area over the acute-angled lateral faces. Therefore it is only possible to detach the clamping contact connection when application takes place of a clearly defined force necessary in order to again open the second contact element. If necessary, there can be a rapid separation of the clamping contact connection, but an undesired, automatic separation of the clamping contact connection is prevented.

Additionally, according to another preferred embodiment, clamping elements are provided on the leg plate so as to prevent a lateral twisting of the second contact element. The clamping elements hold the second contact element in its position, but at any time it is possible to separate the clamping connection, in the aforementioned manner, from the leg plate. Fundamentally said clamping elements can simultaneously serve as holding elements and prevent a sliding back and undesired detachment of the clamping contact connection.

According to another preferred embodiment the second contact element is made from plastic and the maximum opening substantially corresponds to the wedge angle. This ensures that a corresponding contact pressure is present and a good contact is formed between the first and second contact elements. To assist this contact pressure it is also possible to have an openable sheet metal strip arranged in the jaws.

BRIEF DESCRIPTION OF THE DRAWINGS

Further embodiments and advantages of the invention are described in greater detail hereinafter relative to the attached drawings, wherein show:

FIGS. 1a and 1b show the fundamental construction of a clamping contact connection.

FIG. 2 the clamping connection with a device to prevent sliding back.

DETAILED DESCRIPTION OF THE EMBODIMENTS

Figure 3:
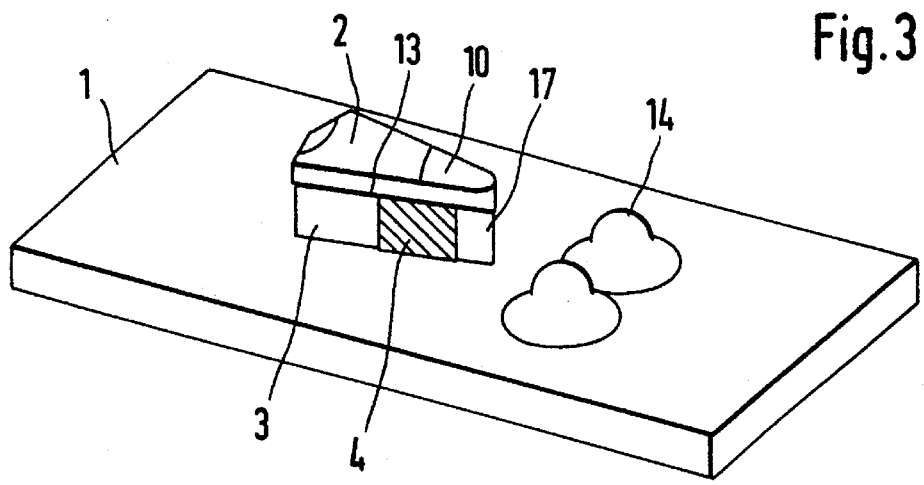
FIG. 3 a diagrammatic representation of the leg plate with a first contact element.

FIG. 1 shows the basic construction of the clamping contact connection according to the invention. FIG. 1a shows the open clamping contact connection and FIG. 1b the closed clamping contact connection. On the diagrammatically represented leg plate 1 is located as the first contact element a wedge 2, which on its two tapering side walls 3 has an outer contact face 4. The wedge 2 is firmly connected to the leg plate 1 and has also in practice electronics and connecting leads to the monitoring device. These are not shown in the drawings and this also applies with respect to the elements with which the leg plate 1 can be fixed to the leg of the mother, because they are generally known. The second contact element 5 has a clamp-like construction and has two openable jaws 6, which pass into a gripping area 7, which serves for the handling of the second contact element. To the second contact element 5 are connected wires 8, which lead to the not shown scalp electrode. On the inside of the jaws 6 are provided contact faces 9, which are insulated from one another and connected to the wires 8. The second contact element 5 is produced in one piece from plastics material, the opening being limited by the maximum bending line of the material and the resilience of the material represents the force which presses the contact faces 9 onto the contact faces 4 of the first contact element 2. The embodiment shown in FIG. 1 is provided with two reciprocally insulated contact faces. Fundamentally it is also possible to have a plurality of different contact faces in the case of a corresponding arrangement and construction of the first contact element 2 and the second contact element 5. The second contact element 5 can also be fixed to the leg plate and the first contact element 2 to the scalp electrode. What is decisive is that the dimensions of the first or second contact element connected to the scalp electrode are such that it can be passed through the inner tube of the introduction aid for fitting to the not shown scalp electrode.

FIG. 1b shows the closed clamping contact connection in which the jaws 6 of the second contact element are in contact with the side walls 3 of the first contact element. The opening of the jaws 6 of the second contact element 5 corresponds to the theoretical bending line of the plastic material, the angle 10 being adapted to the tangent of said theroretical bending line 21, so that the jaws 6 and the side walls 3 are substantially parallel and consequently there is an optimum contacting of the contact faces 4,9. A sliding back of the second contact element 5 from the wedge-shaped first contact element 2 can be prevented by a roughened side wall 3 or additional holding elements.

FIG. 2 shows a possibility for preventing the sliding back of the second contact element 5. The holding device 12, which has a recess 11, whose width is smaller than the width of the gripping area 7 of the second contact element 5, on the one hand prevents the sliding back and on the other prevents a lateral twisting and therefore sliding down of the second contact element 5 from the frist contact element 2. In the embodiment of FIG. 2 the wedge 2 also has a bevelled projecting length 13, which prevents an unintentional upward sliding of the second contact element 5 away from the leg plate 1. The projecting length 13 is bevelled in order to facilitate the desired separation of the clamping contact connection by raising the second contact element 5.

FIG. 3 shows the preferred embodiment with the contact element 2 on the diagrammatically represented leg plate 1 with the contact faces 4 and the bevelled projecting length 13. On the leg plate 1 are also provided plastic material holding elements 14, which prevent a lateral twisting of the second contact element 5 with the clamping contact connection closed. The back 15 of the first contact element hat two surfaces which slope with respect to one another. Fundamentally they can also be straight or curved.

Figure 4A:
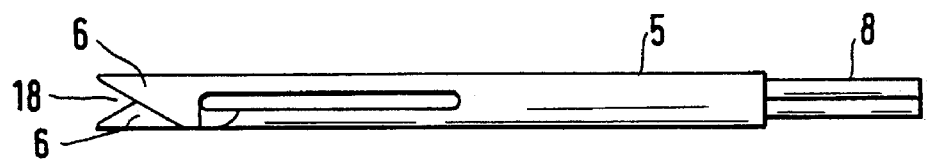
FIGS. 4a, 4b, and 4c a preferred embodiment of a second contact element in different views.
Figure 4B:
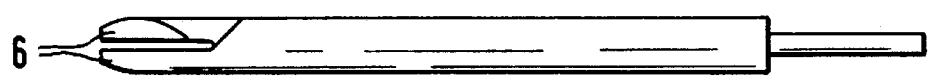
Figure 4C:
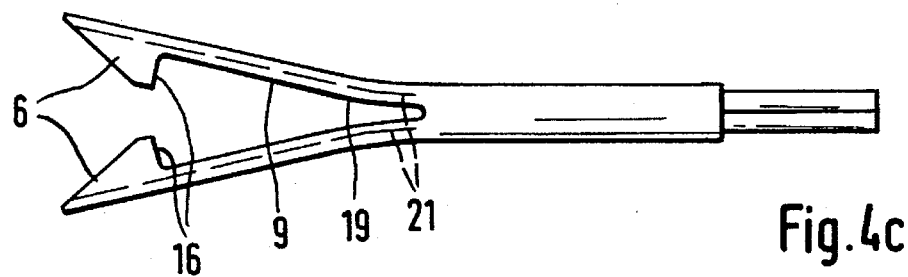

FIG. 4 has a plan view 4a, side view 4b and plan view 4c with opened jaws 6 on the second contact element 5. In the preferred embodiment of the second contact element 2 shown in FIG. 4 hooks 16 are shaped onto the jaws 6 to prevent a sliding back from the frist contact element 2. In the closed state of the jaws 6 the shaped hooks 16 on the front end of the second contact element 5 form a v-shaped depression 18 visible in FIG. 4a, which on assembling the clamping contact connection facilitates the centering on the tip 17 of the second contact element 2 and the opening of the jaws 6. In FIG. 4c on the inside of the jaws 6 is provided a sheet metal band 19 or a spring wire, which has the insulated contact faces 9, to which the wires 8 are connected and which makes an additional contribution to the clamping force due to the spring tension of the sheet metal band. The preferred embodiment for the second contact element, as described relative to FIG. 4. only has two contact faced, because at present no more are necessary. Fundamentally the second contact element can have several jaws 6 with shaped-on hooks 16 and depression 18.

Figure 5:
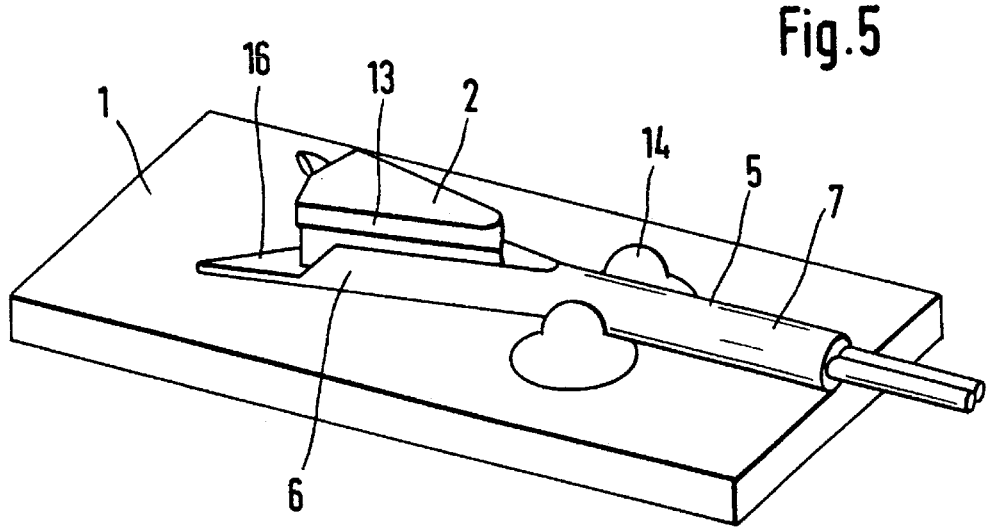
FIG. 5 a clamping contact connection with the elements of FIGS. 3 and 4.

FIG. 5 shows the clamping contact connection with the first contact element according to FIG. 3 and the second contact element according to FIG. 4. In the closed state the side walls 3 with the contact faces 4 are surrounded by the jaws 6 and the hooks 16 are supported on the back 15. This excludes any sliding back of the second contact element 5 from the first contact element 1. An unintentional upward sliding is also prevented by the aforementioned bevelled projecting length 13. The detachment of the clamping contact connection can take place by drawing upwards the second contact element.

Figure 6:
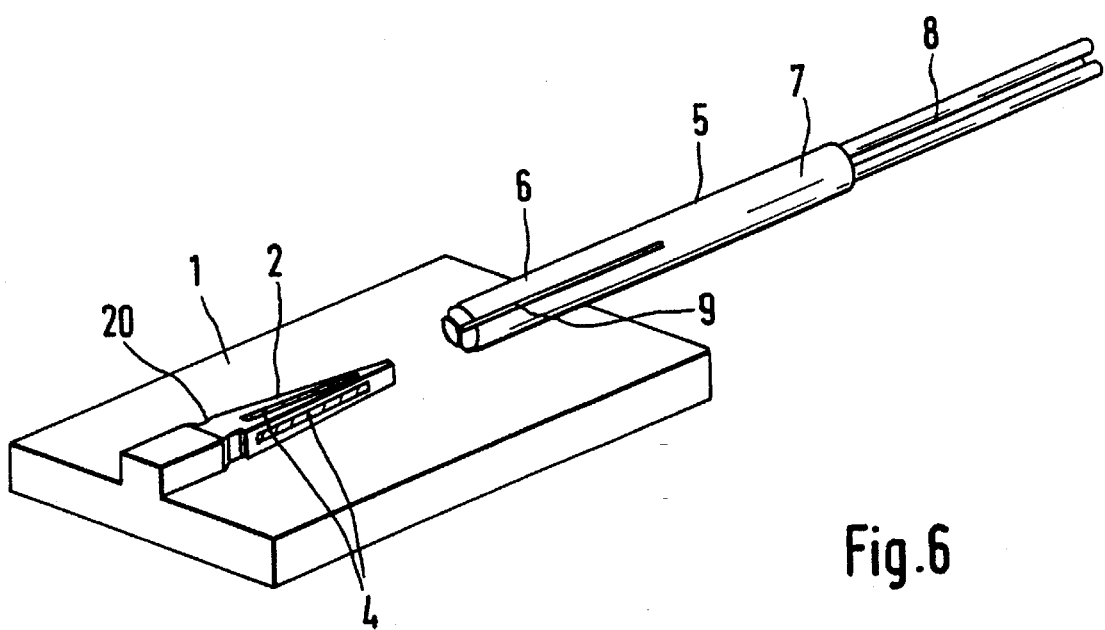
FIG. 6 another embodiment with a wedge-shaped, first contact element having three contact faces.

FIG. 6 shows another embodiment with a first wedge-shaped contact element having three contact faces 4. In this embodiment it is also possible to see that e.g. with a conical design and a spaced arrangement from the surface of the leg plate a plurality of contact faces 4 can be fitted to the first contact element 2. The first contact element 2 shown in FIG. 6 has notches 20 in which can engage the correspondingly constructed hooks on the jaws 6 of the second contact element 5 in order to prevent a sliding from the first contact element 2. As in the previously described embodiments the contact faces 9 are on the inside of the jaws 6 of the second contact element 5, so that there is also a protection against electric shock hazard.

I claim:

1. A clamping contact connection for electrical connection of a fetal scalp electrode to a leg plate that is fixable to an expectant mother, and comprising:

a fetal scalp electrode;

a leg plate;

a first contact element coupled to said leg plate and including a portion which is wedge-shaped or tapers and includes, on said portion, at least two outer contact faces;

a second contact element having at least two openable jaws with inner contact faces, said second contact element connected to the fetal scalp electrode and constructed as an elongated, substantially cylindrical part with a gripping area and a contact area which includes said inner contact faces, the first contact element and the second contact element, when engaged, enabling said jaws of the second contact element to engage said portion of the first contact element, so that the inner contact faces of the second contact element contact the outer contact faces of the first contact element and said jaws prevent an unintentional separation of an inter-connection therebetween.

2. A clamping contact connection according to claim 1, wherein the jaws of the second contact element are shaped to include opposed holding elements.

3. A clamping contact connection according to claim 2, wherein the opposed holding elements are shaped in such a way that when the jaws are closed, a central depression is present between the jaws and which on assembling of the contact elements, facilitates opening of the second contact element.

4. A clamping contact connection according to claim 2, wherein the first contact element is constructed as a wedge, which is fixed to the leg plate and has a plan view substantially corresponding to an acute triangle, including acute-angled side walls and a back, the acute-angled side walls constructed as contact faces and on contacting said second contact element, enable the opposed holding elements to engage the back of the wedge.

5. A clamping contact connection according to claim 4, wherein wedge surface remote from the leg plate, at least in the area of the acute-angled side walls, projects above the same in order to prevent a sliding of the second contact element.

6. A clamping contact connection according to claim 4, wherein the leg plate includes clamping elements which prevent a lateral twisting of the second contact element.

7. A clamping contact connection according to claim 4, wherein the second contact element is made from plastic and the jaws are sufficiently resilient to press the inner contact faces against the outer contact faces.

8. A clamping contact connection according to claim 7, wherein for improving contact pressure, at least one resilient metal strip is positioned between and is openable with the jaws.

\* \* \* \* \*